United States Patent
King

(10) Patent No.: US 7,982,763 B2
(45) Date of Patent: Jul. 19, 2011

(54) PORTABLE PAN-TILT CAMERA AND LIGHTING UNIT FOR VIDEOIMAGING, VIDEOCONFERENCING, PRODUCTION AND RECORDING

(76) Inventor: Simon P. King, Annapolis, MD (US)

(*) Notice: Subject to any disclaimer, the term of this patent is extended or adjusted under 35 U.S.C. 154(b) by 1578 days.

(21) Appl. No.: 11/338,030

(22) Filed: Jan. 24, 2006

(65) Prior Publication Data

US 2006/0119701 A1    Jun. 8, 2006

Related U.S. Application Data

(63) Continuation-in-part of application No. 10/922,597, filed on Aug. 20, 2004, now Pat. No. 7,432,949.

(60) Provisional application No. 60/496,395, filed on Aug. 20, 2003.

(51) Int. Cl.
*H04N 7/14* (2006.01)

(52) U.S. Cl. .............. 348/14.08; 348/14.01; 348/14.02; 600/160

(58) Field of Classification Search .... 348/14.01–14.16, 348/373, 836, 68, 69; 312/209, 312; 600/178, 600/180, 181, 109, 182, 160; 362/287, 418, 362/419, 427; 250/363.08, 368; 378/189, 378/190

See application file for complete search history.

(56) References Cited

U.S. PATENT DOCUMENTS

| | | | | |
|---|---|---|---|---|
| 4,572,594 A * | 2/1986 | Schwartz | ........................ | 312/209 |
| 4,711,541 A * | 12/1987 | Yoshino et al. | ................ | 351/214 |
| 5,088,014 A * | 2/1992 | Boughey | ........................ | 362/132 |
| 5,603,328 A * | 2/1997 | Zucker et al. | ................. | 600/479 |
| 5,712,482 A * | 1/1998 | Gaiser et al. | ............. | 250/363.08 |
| 5,716,126 A * | 2/1998 | Meyer | ............................ | 362/287 |
| 5,931,808 A * | 8/1999 | Pike | ................................ | 604/28 |
| 5,999,749 A * | 12/1999 | Kobayashi et al. | ........... | 396/106 |
| 6,369,847 B1 * | 4/2002 | James et al. | ................ | 348/14.01 |
| 6,464,633 B1 * | 10/2002 | Hosoda et al. | ................ | 600/178 |
| 6,485,413 B1 * | 11/2002 | Boppart et al. | ............... | 600/160 |
| 6,633,328 B1 * | 10/2003 | Byrd et al. | ...................... | 348/143 |
| 7,443,417 B1 * | 10/2008 | Heinrich | ......................... | 348/66 |
| 2002/0087047 A1 * | 7/2002 | Remijan et al. | ................ | 600/109 |
| 2003/0093503 A1 * | 5/2003 | Yamaki et al. | ................ | 709/220 |
| 2004/0264175 A1 * | 12/2004 | Willoughby | .................. | 362/105 |

* cited by examiner

*Primary Examiner* — Melur Ramakrishnaiah
(74) *Attorney, Agent, or Firm* — Ober, Kaler, Grimes & Shriver; Royal W. Craig

(57) ABSTRACT

The present invention is a portable camera and lighting unit for standalone use in videography to create a high-resolution well-illuminated video feed from a vast array of camera angles and positions, the illumination source always inherently tracking with the camera. The unit may also be used as a satellite in combination with a primary video conferencing and production station (VVPR) for multi-camera production and teleconferencing capabilities. The portable camera and lighting unit includes a portable base, a mast extending upward from the base, and an articulating boom that is fully-pivotable and extendable. A remote control Pan-Tilt-Zoom camera is mounted at the end of the boom for overhead images of healthcare procedures, and an adjustable beam light source is mounted directly on the camera for lighting. The mast is equipped with a color monitor coupled to the camera for operator previewing at the portable unit, and the remote control camera provides a single video feed that can be teleconferenced, recorded, and even mixed with other cameras when used as a satellite adjunct to the primary VVPR, thereby allow full production capabilities for live interactive broadcasts, all in real time by a single operator from a single point of control. The portable unit is mobile and offers more diverse lighting and camera angles than previously possible.

13 Claims, 6 Drawing Sheets

PORTABLE PAN-TILT CAMERA AND LIGHTING UNIT FOR VIDEOIMAGING, VIDEOCONFERENCING, PRODUCTION AND RECORDING

CROSS-REFERENCE TO RELATED APPLICATION(S)

The present application is a continuation-in-part related to U.S. patent application Ser. No. 10/922,597 filed Aug. 20, 2004, now U.S. Pat. No. 7,432,949 which in turn derived priority from U.S. provisional application Ser. No. 60/496, 395, filed Aug. 20, 2003.

BACKGROUND OF THE INVENTION

1. Field of the Invention

The present invention relates to videoimaging systems and, more specifically, to a portable pan-tilt camera and lighting unit for videoimaging, videoconferencing, production, lighting and recording. The portable camera and lighting unit can be used to provide a standalone video feed and/or lighting source, or can be used as a satellite camera and lighting unit for use in conjunction with station for surgical videoimaging ("VVPR") such as shown and described in U.S. patent application Ser. No. 10/922,597. The portable camera and lighting unit disclosed herein improves the resolution of video and lighting at any location including hospital operating room/procedure rooms, field locations, or other remote locations for purposes of sourcing audio, video and data communications there from for education, consulting, surgical assistance, diagnostics, demonstrations, and the like.

2. Description of the Background

There are many geographic areas where rural physicians and health practitioners need continuing education, and possibly real-time guidance from experts in carrying out various surgical procedures.

Situations calling for real-time video production capabilities are quite apparent, for example, some level of video production services are commonly required in medical settings, including academic surgical procedural programs to be used in teaching students, or surgical procedural/promotional programs for medical devices, instructional & assembly programs for mapping out the steps for assembling or using a complicated apparatus, seminar & workshop capture, patient education programs & documentary, sales force motivational programs, etc. Indeed, many surgeries are now broadcast by live event video production and internet broadcasting or satellite uplink. Both recorded program production as well as live event productions require extensive production overhead. Unfortunately, distance and limited resources make it increasingly complicated for providers to furnish these services.

While medical video production services are available, they are usually in the form of a conventional video crew. The crew (4-10 people) equip an operating room with video cameras, microphones, video mixers, audio mixers, monitors, hundreds of feet of cables, and tape or broadcast the surgery. The work product of the various cameras and crewmen may be broadcast and recorded in real time or turned over to an editor for mixing, editing, to generate a final edited master recorded on tape/digital tape/CD/DVD There have been few attempts to consolidate the process in the surgical setting to make it less obtrusive, more flexible in serving all the foregoing needs, and more economical to health care providers. One effort is described in United States Patent Application No. 20030142204 by Rus, Steven H. filed Jul. 31, 2003. This application discloses a surgical lighting control and video system that gives a user access to multiple devices at one station and makes control of the system simpler and more intuitive. A graphical LCD display is used to control a plurality of devices, such as overhead lighting, ambient lighting, cameras, and other operating room accessories. A voice interface allows the surgeon to adjust lighting and other aspects by simply speaking. A foot pedal interface and an infra-red remote control interface grant the surgeon control of the cameras, enabling direct control of rotate and zoom functions of the camera.

Surgeons generally are not capable or willing to attend to all of their own video recording/teleconferencing/production needs themselves while indisposed with a patient. A better solution is a mobile videoimaging, videoconferencing and production station capable of being manned by a single trained person, such as shown and described in U.S. patent application Ser. No. 10/922,597 filed Aug. 20, 2003 by the present inventors. The VVPR system described therein provide high-resolution interactive audio, video and data communications between hospital operating room/procedure room environments and other remote locations for education, consulting, remote surgical assistance, diagnostics, demonstrations, and the like.

It has since been found that tremendous enhancements can be attained by use of a portable camera and lighting unit having a remotely-controlled video camera and light source (particularly an adjustable high-intensity light source such as fiber optic or the like) sharing the same optical path, both mounted on an articulating boom for videoimaging, videoconferencing, production and recording. The present invention provides these capabilities in the form of portable camera and lighting unit combining a pan-tilt video camera with directional lighting source sharing the same optical path, the unit being capable of providing a standalone video feed, or being suited for use as a satellite unit for use in conjunction with a primary surgical videoimaging station ("VVPR") such as shown and described in applicant's above-cited application. In both cases the present portable camera and lighting unit improves the flexibility, resolution and diverse camera angles and lighting to improve the interactive video and data production and communications capabilities between hospital operating room/procedure room environments and other remote locations for education, consulting, surgical assistance, diagnostics, demonstrations, and the like.

SUMMARY OF THE INVENTION

It is therefore an object of the present invention to provide a portable pan-tilt video camera and lighting unit for video imaging and production in many different applications, such as medical/surgical imaging, engineering and remote diagnostics, video conferencing, etc.

It is another object to provide a portable pan-tilt camera and lighting unit incorporating a remotely-controlled pan-tilt video camera as well as an adjustable-beam light source sharing the same optical path, both mounted on an articulating boom for videoimaging, videoconferencing, production and recording.

It is still another object to provide a portable camera and lighting unit controllable by a single trained person to provide complete control over high-resolution video capture and lighting therefor, for real time video communications between diverse locations such as hospital operating room/procedure room environments and other remote locations for education, consulting, remote surgical assistance, diagnostics, demonstrations, and the like.

It is still another object to provide a satellite camera and lighting unit as described above that is suited for providing a standalone video feed, or alternatively, that integrates seamlessly with the primary surgical videoimaging station ("VVPR") as shown and described in applicant's above-cited co-pending application, the portable unit communicating directly and being controlled by the VVPR for multi-camera surgical videoimaging all controllable by a single trained person to provide a complete array of audio and high-resolution video capture tools, mixing and editing tools, recording capabilities to a variety of common analog and digital formats, and real time video and data communications capabilities for networked communications for teleconferencing between hospital operating room/procedure room environments and other remote locations for education, consulting, remote surgical assistance, diagnostics, demonstrations, and the like.

It is another object to provide a portable camera and lighting unit as described above which is contained in a portable base with fully articulating boom-mounted video camera for high-resolution close-up surgical imaging from multiple camera angles.

It is still another object to provide a portable camera and lighting unit suitable for use in an operating room environment, and for convenient wheeled positioning between operating rooms in a hospital.

In accordance with the foregoing objects, the present invention is a portable pan-tilt camera and lighting unit for standalone use, or for use in combination with an existing mobile videoimaging, videoconferencing, production and recording (VVPR) system for surgical imaging such as shown and described in applicant's co-pending U.S. patent application Ser. No. 10/922,597. The portable camera and lighting unit according to the invention allows enhanced multi-angle high-resolution video and lighting for video feeds between any diverse locations such as hospital operating room/procedure room environments and other remote locations for education, consulting, surgical assistance, diagnostics, demonstrations, and the like.

The present invention comprises a portable base, a mast extending upward from the base, and an articulating boom that is fully-pivotable and extendable. A remote control Pan-Tilt-Zoom camera is mounted at the end of the boom for overhead images of healthcare procedures, and an adjustable-beam light source is mounted proximate the camera lens directed along the same optical path as the camera, thereby providing consistent variable-beam-width lighting no matter the camera angle. The mast is equipped with a 6.4" TFT color monitor coupled to the camera for operator previewing at the portable unit.

The portable camera and lighting unit may be used alone to provide a single standalone video feed with lighting, or may be used in combination with a VVPR station as described in U.S. patent application Ser. No. 10/922,597 filed Aug. 20, 2003 by the present inventors, or any other operating room videoimaging and production solution. In the case the VVPR, the present invention integrates directly with the mobile VVPR station, which generally comprises a video camera and lighting system mounted on a mobile platform, the platform including an articulating boom assembly mounted on a wheeled cabinet enclosure, an array of video production equipment inside the cabinet, an array of teleconferencing equipment inside the cabinet, and a fail-safe battery system in the cabinet for powering the foregoing. The video production equipment offers an array of audio and high-resolution video capture tools, mixing and editing tools, recording capabilities to a variety of common analog and digital formats, and real time video and data communications capabilities for networked communications for teleconferencing between hospital operating room/procedure room environments and other remote locations for education, consulting, remote surgical assistance, diagnostics, demonstrations, and the like.

BRIEF DESCRIPTION OF THE DRAWINGS

Other objects, features, and advantages of the present invention will become more apparent from the following detailed description of the preferred embodiment and certain modifications thereof when taken together with the accompanying drawings in which.

DETAILED DESCRIPTION OF THE PREFERRED EMBODIMENTS

The present invention is a portable pan-tilt camera and lighting unit for standalone use in obtaining a well-lit high-resolution video feed during videoimaging. Alternatively, the device may be used as a satellite unit in combination with virtually any other existing videoimaging solution, including a mobile videoimaging, videoconferencing, production and recording (VVPR) station as shown and described in U.S. patent application Ser. No. 10/922,597 filed Aug. 20, 2003 by the present inventors. Satellite use in conjunction with the VVPR adds a complete array of audio and high-resolution video capture tools, mixing and editing tools, recording capabilities to a variety of common analog and digital formats, and real time video and data communications capabilities for networked communications for teleconferencing between hospital operating room/procedure room environments and other remote locations for education, consulting, remote surgical assistance, diagnostics, demonstrations, and the like.

Whether used alone or as a satellite, the portable camera and lighting unit is designed for direct control by a single trained person during videoimaging to provide a self-contained lighting solution and to form a real time video feed for networked communications and teleconferencing between hospital operating room/procedure room environments and other remote locations for education, consulting, remote surgical assistance, diagnostics, demonstrations, and the like.

Figure 1:
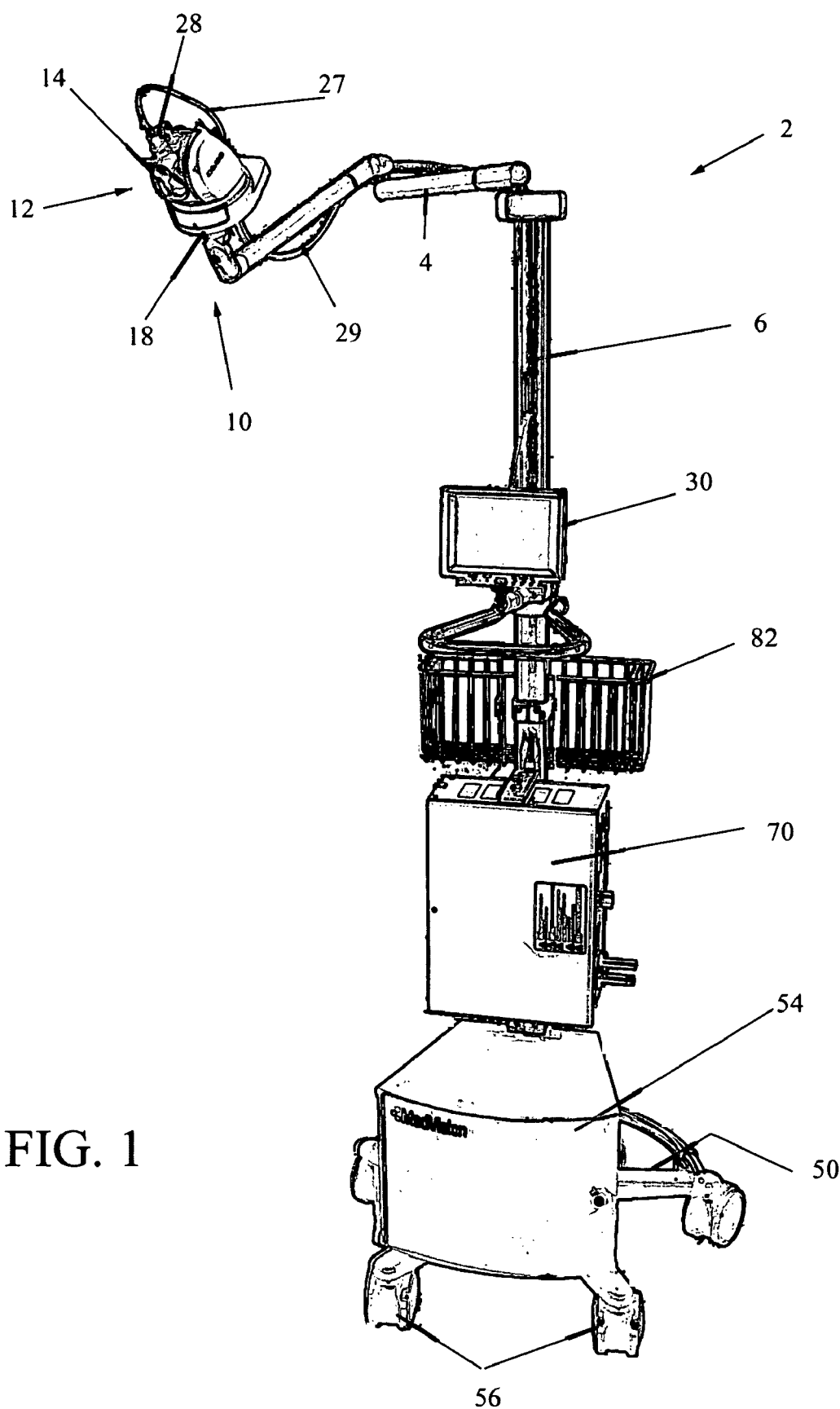
FIG. 1 is a perspective view of the portable camera and lighting unit 2 according to the present invention.

FIG. 1 is a front perspective view of the portable camera and lighting unit 2. Portable camera and lighting unit 2 generally comprises a fully-articulated video camera and lighting system 10 (to be described) mounted on an articulating boom 4, which is in turn mounted on a support mast 6 that extends upwardly from a mobile platform 50. A cabinet 54 is mounted on the platform 50, and the cabinet 54 encloses a four-outlet power strip connected to an isolation transformer (optional) for powering the articulated video camera and lighting system 10.

The wheeled mobile platform 50 supports the cabinet 54 (enclosing a power strip and isolation transformer) as well as a support mast 6 that protrudes upward at the rear of cabinet 54. The support mast 6 leads to a fully-articulating telescoping boom 4 mounted there atop, and pan-tilt camera and lighting system 10 is mounted distally thereon. The pan-tilt camera and lighting system 10 comprises a remote control Pan-Tilt-Zoom camera 12 for overhead images of healthcare procedures, and an adjustable-beam light source which, in the illustrated preferred embodiment is a fiber-optic light source 70 directed through a fiber-optic light source projection lens 14 for illuminating camera shots. One skilled in the art will understand that other light sources may be suitable such as LEDs, fluorescent or incandescent, as desired. The fiber optic light source projection lens 14 is mounted directly proximate the lens of the Pan-Tilt-Zoom camera 12 (as will be described) to direct a focused light beam along the same path as the camera image. Thus, the Pan-Tilt-Zoom camera 12 is capable of providing continuously illuminated overhead images of healthcare procedures. The fiber optic light source projection lens 14 is optically coupled to the fiber-optic light source 70, the light source 70 being mounted via a bracket directly to the lower extent of mast 6. The remote control camera 12 includes a base which is mounted by screw threads 18 directly to the distal end of boom 4 thereby providing additional angle capability to supplement the camera's inherent remote control pan/tilt/zoom capabilities. Remote control camera 12 may be controlled remotely from an infrared controller, from a joystick mounted on the portable unit 2, or from the VVPR (not shown). Likewise, the camera 12 output may be connected to any NTSC receiver, or to the mixing and video production equipment in the VVPR as well as the teleconferencing and networking equipment. In addition to the single remote control camera 12, the portable camera and lighting unit 2 is capable of mounting additional cameras if desired.

The portable camera and lighting unit 2 is designed to be manned and controlled remotely by a single operator and, even when used in conjunction with the VVPR (which has additional remote control cameras), all can be controlled by a single operator rather then a full production crew as typically required using conventional means.

A preview panel 30 comprising a small color monitor is pivotally mounted on the mast 6 for operator previewing when in proximity of the portable unit 2.

A basket 82 is mounted on the mast 6 for organization purposes.

The boom 4 and mast 6 stem from the wheeled mobile platform 50, the mast 6 being anchored in the platform 50 and secured behind the cabinet 54 for additional support and stabilization. The cabinet enclosure 54 includes a front door for access to the isolation transformer. The platform 50 is supported on castors 56 for mobility, and at least two of the five castors 56 are locking castors for stationery positioning.

Figure 2:
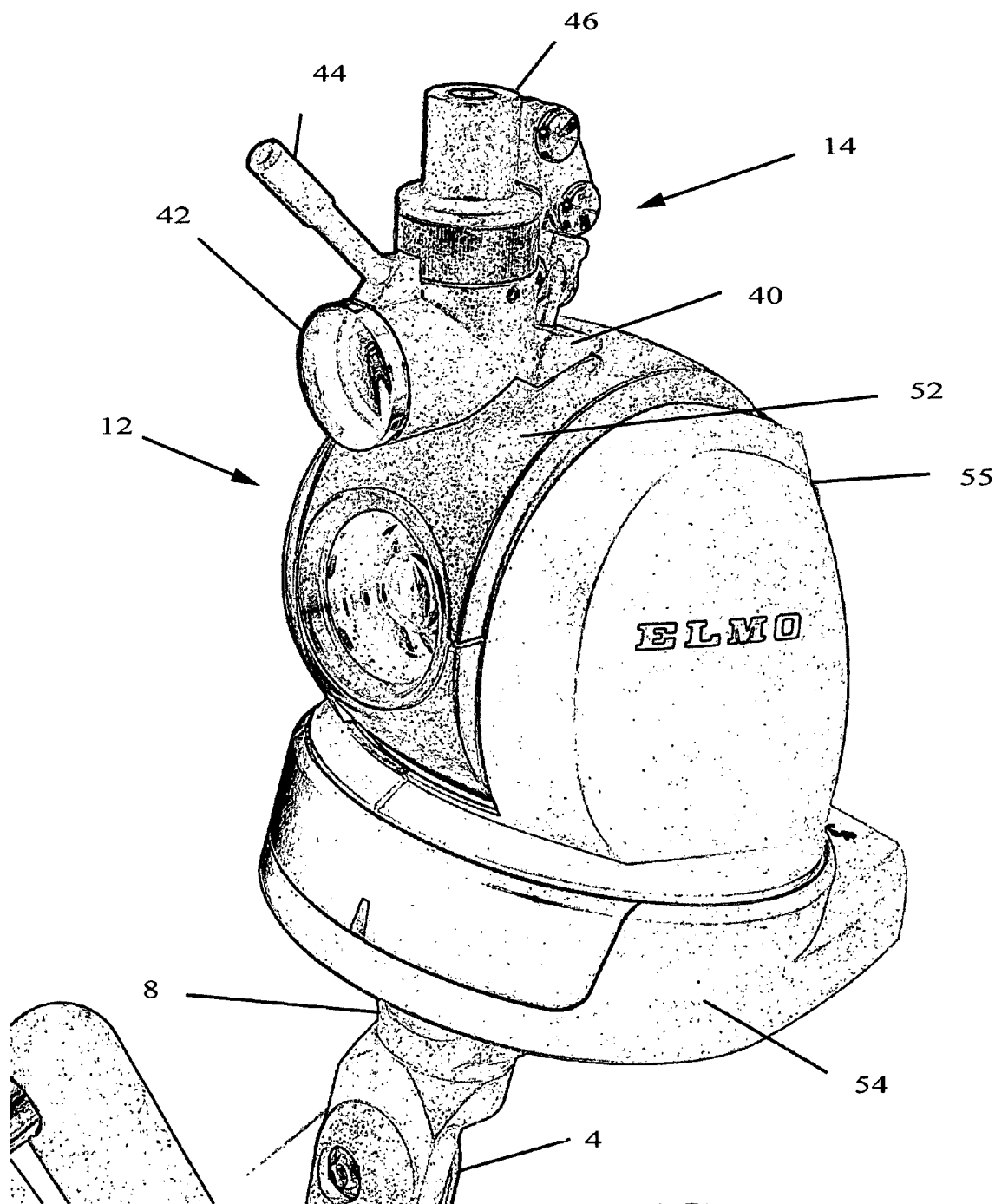
FIG. 2 is a perspective view of the Pan-Tilt-Zoom camera 12 and fiber optic light source projection lens 14 mounted at the end of the boom 4 for overhead images.

FIG. 2 is a perspective view of the Pan-Tilt-Zoom camera 12 and fiber optic light source projection lens 14 mounted at the end of the boom 4 for overhead images. Camera 12 is presently a model PC110R1 Elmo video camera mounted via screw-threads 18 directly to the distal end of boom 4. The camera 12 is connected by conventional cables 29 coupled by connector 28 leading in from the backside (see FIG. 1), the cables 29 running down the length of boom 4 to the floor (and, if desired, over to the VVPR system). The camera 12 may be controlled individually by a controller mounted on the satellite unit 2, by a wireless remote controller, or may be commonly controlled by the camera controller in the VVPR system (which includes a hardwired Telemetrics, Inc. Mahwah, N.J. Model CP-ITV-VCC-4 142 for common control of up to four cameras inclusive of camera 12 as well as those in the VVPR). Additionally, the VVPR also includes a wireless remote controller, and a camera selector for push-button selection of the active camera, which may include camera 12 in the portable unit 2.

In the illustrated embodiment, the adjustable-beam fiber-optic projection lens 14 comprises a fiber optic receptacle 46 for detent-insertion of a fiber optic cable 27 (see FIG. 1), receptacle 46 angling to an adjustable lens 42 for concentrating or diffusing the output light beam. Adjustable lens 42 is manually adjusted by a thumb-screw 44. Fiber optic light source projection lens 14 is mounted atop the lens carriage 52 of the Pan-Tilt-Zoom camera 12 via a bracket 40 which is screwed thereto from the underside of the lens carriage (this may be accomplished by disassembly of the camera 12). The Pan-Tilt-Zoom camera 12 is remotely controlled by electrical cable 29, the lens carriage 52 rotating about a horizontal axis, and the body of camera 12 being seated on a rotating base 54 for rotation about a vertical axis. This provides fully articulated two-axis adjustment of the lens of camera 12. The adjustable lens 42 of projection lens 14 is fixed to point along the exact same optical viewing path of camera 12, and since the fiber optic light source projection lens 14 is fixedly attached to the lens carriage 52 the adjustable lens 42 of fiber optic light source projection lens 14 will always be directed along the same optical viewing path of camera 12 regardless of the remote controlled orientation of the camera 12 lens. This is an extremely important feature for well-illuminated surgical imaging. As seen in FIG. 2, the body 55 of the illustrated Elmo™ camera 12 needs to be machined slightly to fully accommodate the bracket 40 when the lens carriage 52 is rotated fully backward. The machining simply enlarges the notch in the body to give full backward freedom of movement. This step is not necessary with some other camera makes and models, such as Sony™.

Figure 3:
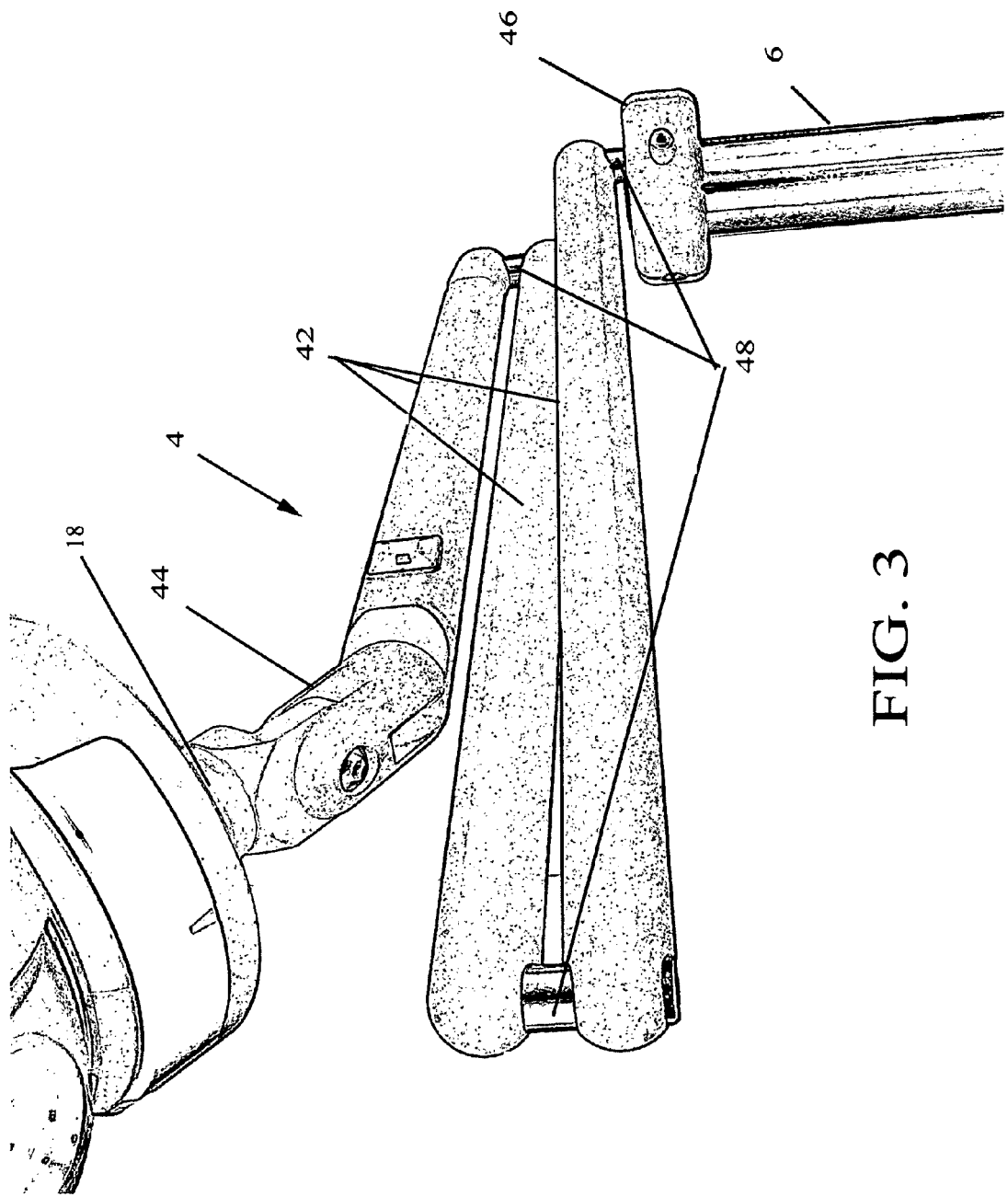
FIG. 3 is a perspective view of the boom 4.

FIG. 3 is a perspective view of the boom 4 which comprises a plurality of lengths of aluminum tubing 42 pivoted endwise at pivots 48 as shown, each length of tubing 42 being approximately 22" in length. While two lengths of tubing 42 are adequate for most purposes, three may be preferred where longer extensions are helpful. With three lengths 42 in a fully extended position the boom 4 will stretch 60" outward, with two lengths 40", and in a retracted position just 22". The boom 4 is capable of articulating to any intermediate position. The boom 4 is mounted to the top of mast 6 by a collar 46 which screw-clamps the mast 6. A universal joint 44 is pivotally attached at the distal end of the outermost section of tubing 42, and the camera 12 is attached to the universal joint 44 directly via a screw threaded post 18. The mast 6 extends upward 62", thereby giving the boom 4 easy deployment within a 10 foot diameter.

Figure 4:
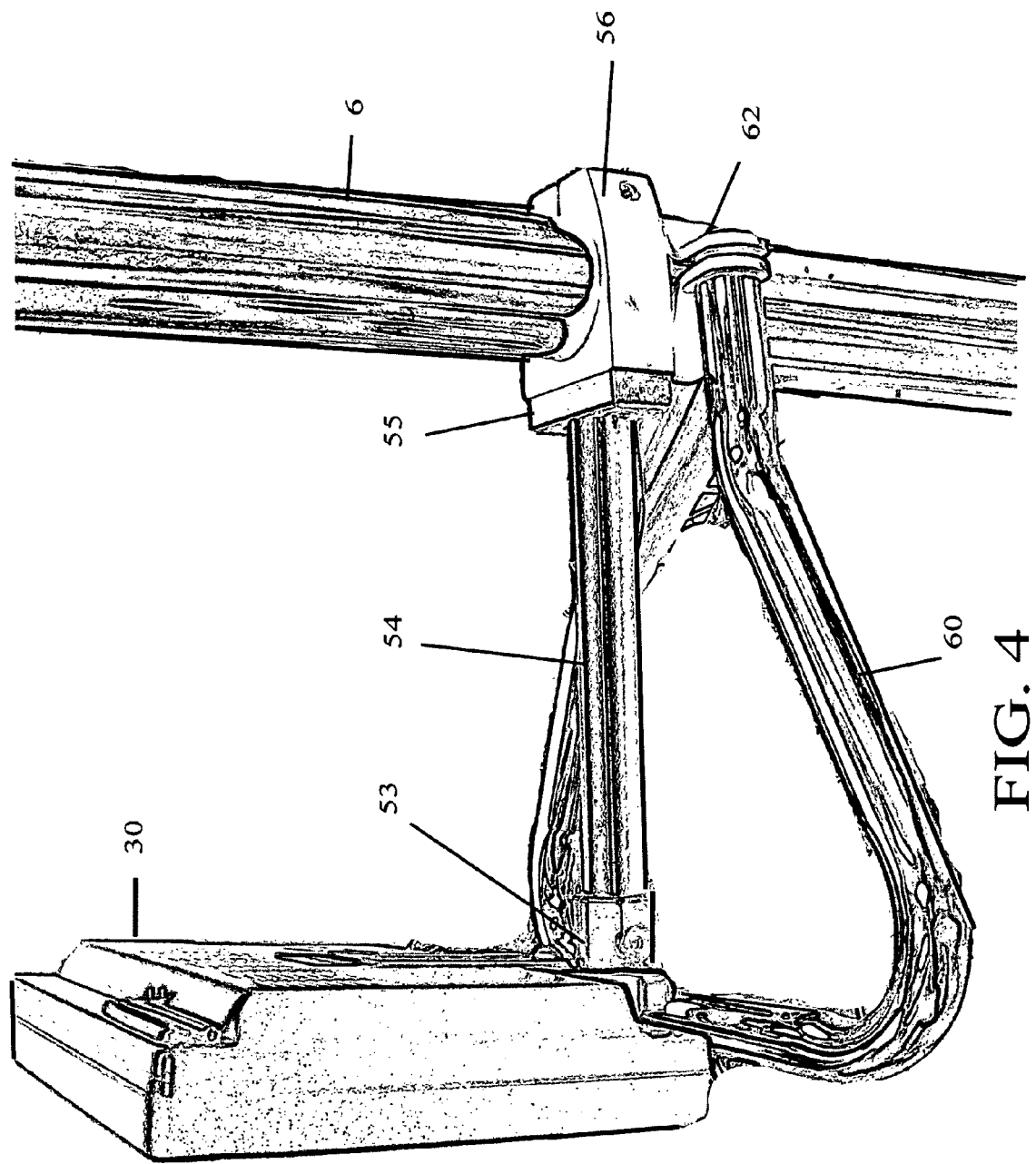
FIG. 4 is a close-up view of the preview panel 30.

FIG. 4 is a close-up view of the preview panel 30 which comprises a small color monitor pivotally mounted on the mast 6 for operator previewing. The preview panel 30 comprises a small 6.4" color monitor with NTSC input cable branched to the output of camera 12 for active broadcast monitoring. A suitable preview panel 30 is a TFT LCD such as a 6.4" TFT LCD, Model LCD-640 by Tote Vision, Inc. The preview panel 30 is mounted on a pivoting collar 53 distally mounted on a short section of extension tube 54 (approximately 1.5'), the extension tube 54 running to a flange 55 that is screw-attached to a yoked compression fitting 56 that secures around mast 6.

A pull handle 60 is similarly attached by a yoked compression fitting 62 that secures around mast 6, directly beneath preview panel 30. Pull handle 60 facilitates easier one-handed maneuvering of the portable unit 2.

The mast 6 is a fixed-height 2" diameter stainless steel tube that is supported in a yoke inside the mobile platform 50.

Figure 5:
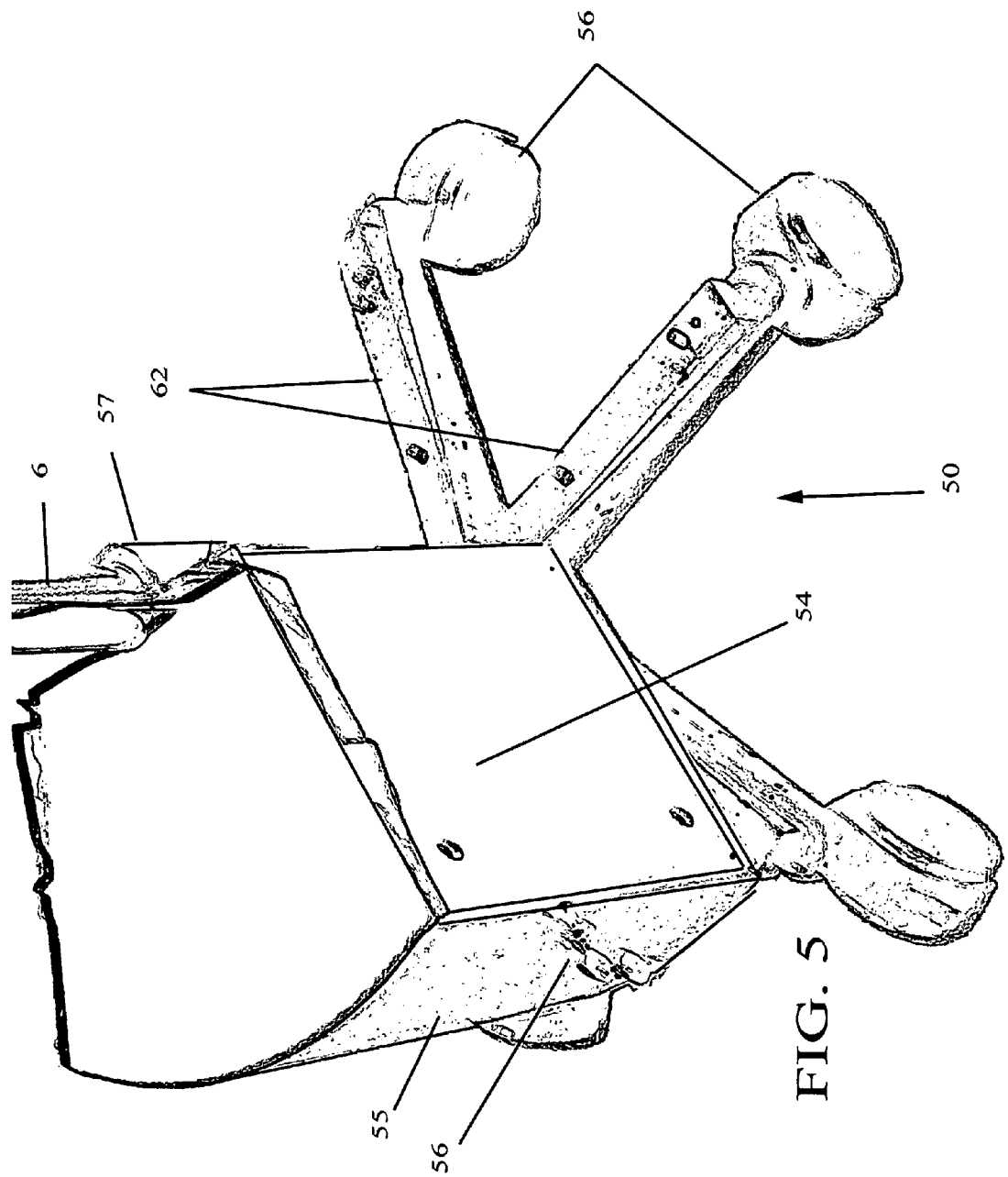
FIG. 5 is a close-up view of the wheeled mobile platform 50 with cabinet 54 enclosing a plug-in power strip/receptacle connected to an optional isolation transformer (recommended for biomedical applications), which in turn powers the on-board components.

FIG. 5 is a close-up view of the wheeled mobile platform 50 with cabinet 54 which encloses the power strip and isolation transformer, with support mast 6 protruding upward from the rear of cabinet 54. The wheeled mobile platform 50 comprises a unitary carriage with five protruding legs 62 converging to a center point, each of the five legs 62 bearing a castor 56. The mast 6 is inserted into a receptacle at the center point of platform 50 for proper balance, and the bottom of the mobile platform 50 is preferably counterweighted to prevent tipping over due to the weight of the extended boom 4. A 25 lb offset weight is sufficient, and this may be a lead weight cast into the legs of the mobile platform 50.

The cabinet 54 is bolted to the mobile platform 50 in advance of the mast 6, and this further comprises a six-walled enclosure with hinged front panel 55 and keyed lacking latch 56. A yoke bracket 57 is bolted to the back of the cabinet 54 and provides additional support for the mast 6 which passes upward there through. The five legs 62 of platform 50 each with castor 56 allows effortless repositioning of the portable unit 2 at the surgery site.

Referring back to FIG. 1, the fiber optic light source projection lens 14 is optically coupled to a fiber-optic light source 70 which is bracketed directly to the mast 6 just above the cabinet 54 as shown. Though various light sources may suffice as described above, the presently preferred light source 70 is fiber optic CUDA™ XLS-300 300 Watt Xenon light source.

The power strip (not shown) mounted in the cabinet may comprise a conventional four-outlet fuse-protected power strip, with electrical cord passing outward from the back of cabinet 54. The power strip is connected to a 120 vac isolation transformer (also not shown) housed inside the cabinet 54 for overvoltage/overcurrent protection, and this powers all 120 vac equipment (namely, the fiber optic light source 70 which is plugged directly therein). The isolation transformer is an optional component but affords a more desirable level of protection in sensitive surgical/medical settings. The power strip may be connected to a 120 vac standard wall receptacle, or over to the VPPR which includes two safety-sealed 12 volt lead-acid batteries for battery operation.

Figure 6:
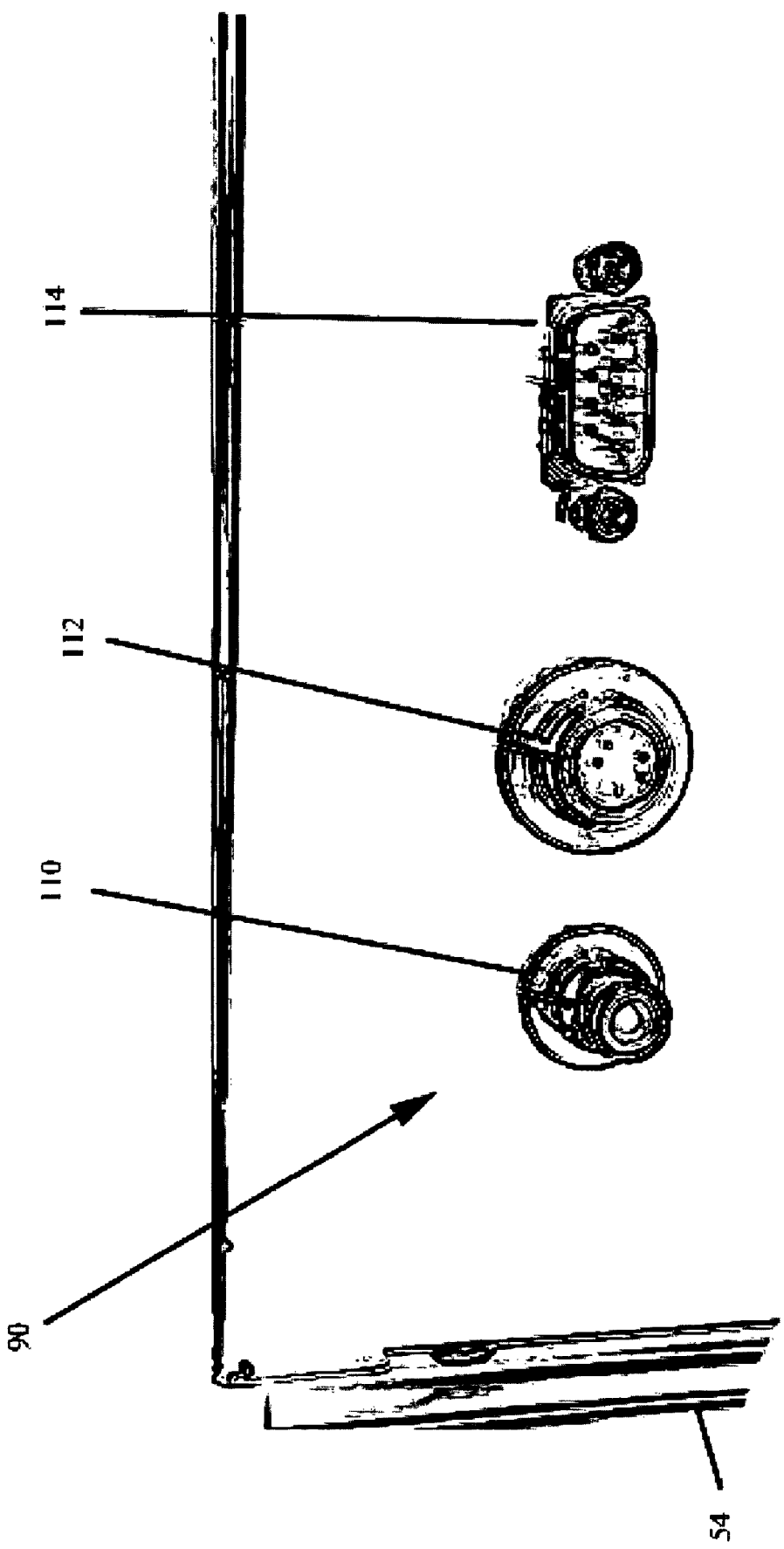
FIG. 6 is a close-up view of the input/output panel 90 at the rear of cabinet 54.

FIG. 6 is a close-up view of the input/output panel 90 at the rear of cabinet 54 which provides easy access to appropriate jacks for inputting/outputting S-video 110, composite video 112, and/or serial control signals via a CAT-5 cable connector 114 for DDC and control signals to/from any Digital Video Interface compliant device to/from the Pan-Tilt-Zoom camera 12.

In use, the portable camera and lighting unit 2 is wheeled and parked (and, if used as a VVPR satellite, the VVPR is likewise wheeled and parked at an opposing location, such as across the room). The boom 4 is extended and angularly positioned as desired to position the camera 12 directly overhead the operating site. Likewise, fiber-optic projection lens 14 is adjusted to illuminate the entire camera field of view. These adjustments are then fine-tuned by remote control positioning of the camera 12 lens. With camera 12 in place, the operator pivots his preview panel 30 to provide the surgical team or other onlookers with preview capability. As the surgery proceeds, the operator can control the single live video feed and illumination therefore to provide a live high resolution video feed for networking, teleconferencing, and/or recording. If connected to the VVPR full production capabilities are added, and the operator can multiplex the camera signals from the portable unit 2 with those of the VVPR and produce in any known format such as Mini-DV, S-VHS, VHS and DVD recordings for the surgeon to leave with a copy to present at his/her next presentation if desired.

The portable camera and lighting unit 2 set forth above excels at providing a standalone high-resolution well-illuminated video feed from a vast array of camera angles and positions, the illumination source always inherently tracking the camera. Moreover, the portable unit integrates seamlessly with virtually any primary surgical videoimaging solution, including the VVPR such as shown and described in applicant's above-cited application, thereby providing full conferencing and production capabilities. In both cases the present portable camera and lighting unit improves the flexibility, resolution and diverse camera angles of the interactive video and data production and communications between hospital operating room/procedure room environments and other remote locations for education, consulting, surgical assistance, diagnostics, demonstrations, and the like. Imaging can be accomplished by a single trained operator, replacing the traditional team of videographers.

Moreover, the portable camera and lighting unit 2 has a footprint well-suited for enclosed environments (such as hospital operating rooms), all power components are safely contained in an aesthetically-pleasing base cabinet, and the fully-articulating boom-mounted video camera gives high-resolution close-up imaging for a myriad of applications.

Having now fully set forth the preferred embodiments and certain modifications of the concept underlying the present invention, various other embodiments as well as certain variations and modifications thereto may obviously occur to those skilled in the art upon becoming familiar with the underlying concept. It is to be understood, therefore, that the invention may be practiced otherwise than as specifically set forth herein.

I claim:

1. A mobile videoimaging and lighting unit for producing a live video feed, comprising:
    a wheeled base;
    a cabinet mounted on said base;
    a mast extending vertically from said cabinet;
    an articulating boom extending from atop said mast;
    a remotely-controlled pan-tilt-zoom video camera mounted distally on said boom, said video camera having a lens supported in an articulating lens carriage, a body pivotally supporting said articulating lens carriage, and a base rotatable supporting the body of said video camera, said base being fixedly attached to said boom, and said articulated body and lens carriage providing two-axis remote control of an optical path of said lens and video camera; and
    a light source attached to the lens carriage of said video camera for directing a beam of light along the same optical path shared by said video camera;
    whereby said remote mobile videoimaging unit may be wheeled into a convenient location in an operating room or other environment and controlled by a single operator for producing a live video feed.

2. The mobile videoimaging and lighting unit according to claim 1, wherein said light source further comprises an adjustable-beam projection lens attached to the lens carriage of said video camera for directing an adjustable beam of light along the same optical path shared by said video camera, and a light-generating source coupled to said projection lens.

3. The mobile videoimaging and lighting unit according to claim 2, wherein said light-generating source further comprises a fiber optic lighting source optically coupled to said projection lens.

4. The mobile videoimaging and lighting unit according to claim 3, wherein said fiber optic light-generating source is mounted on said mast and is coupled to said projection lens by an optical cable.

5. The mobile videoimaging and lighting unit according to claim 2, further comprising an isolation transformer mounted in said cabinet and electrically connected to said fiber optic light-generating source.

6. The mobile videoimaging unit according to claim 1, further comprising a color video display mounted on said mast and connected to said remotely controlled video camera for displaying an output from the remotely-controlled video camera to an operator.

7. The mobile videoimaging and lighting unit for producing a live video feed, comprising:
   a wheeled base;
   a cabinet mounted on said base;
   a mast extending vertically from said base;
   an articulating boom extending from atop said mast, said boom further comprising a plurality of fixed segments pivotally attached end-to-end;
   a remotely-controlled articulating pan-tilt-zoom video camera mounted distally on said boom, said video camera having a lens supported in an articulating lens carriage, a body supporting said lens carriage, and a base rotatable supporting the body of said video camera, said base being fixedly attached to said boom, and said articulated body and lens carriage providing two-axis remote control of an optical path of said lens and video camera;
   a fiber-optic projection lens attached to the lens carriage of said video camera for directing a beam of light along the same optical path shared by said video camera;
   a fiber optic lighting source optically coupled to said projection lens;
   a color video display mounted on said mast and connected to said remotely controlled video camera for displaying an output from the remotely-controlled video camera to an operator; and
   a source of power for powering the fiber optic light-generating source and color video display.

8. The mobile videoimaging and lighting unit according to claim 7, wherein said fiber optic projection lens is an adjustable-beam projection lens attached directly to the lens carriage of said video camera for directing an adjustable beam of light along the same optical path shared by said video camera.

9. The mobile videoimaging and lighting unit according to claim 8, wherein said fiber optic light-generating source is mounted on said mast and is coupled to said projection lens by an optical cable.

10. In combination with an existing mobile videoimaging unit for control by a single operator to produce a live video feed, a remote mobile videoimaging unit, comprising:
    a wheeled base;
    a cabinet mounted on said base;
    a mast extending vertically from said base;
    an articulating boom extending from a top of said mast, said boom comprising at least two fixed segments pivotally attached end-to-end;
    a remotely-controlled pan-tilt-zoom video camera mounted distally on one end of said boom, said video camera having a lens supported in an articulating lens carriage, a body supporting said lens carriage, and a base rotatable supporting the body of said video camera, said base being fixedly attached to said boom, and said articulated body and lens carriage providing two-axis remote control of an optical path of said lens and video camera;
    a fiber-optic projection lens attached to the lens carriage of said video camera for directing a focused beam of light along the same optical path shared by said video camera;
    a light source for supplying light through the projection lens; and
    an electrical cable connecting the remote mobile videoimaging unit to said existing mobile videoimaging unit for common control by a single operator from said mobile videoimaging unit to produce a live video feed.

11. The mobile videoimaging unit according to claim 10, wherein said mobile videoimaging unit further comprises a color video display mounted on said mast for displaying an output from the remotely-controlled video camera to an operator.

12. A mobile lighting unit for producing lighting for a live video feed of a medical procedure, comprising:
    a wheeled base;
    a cabinet mounted on said base;
    a mast extending vertically from said base;
    an articulating boom extending from atop said mast said boom comprising at least two fixed segments pivotally attached end-to-end; and
    an adjustable-beam fiber-optic projection lens mounted distally on said boom;
    a fiber optic light-generating supply mounted on said mast;
    an optical cable connecting said fiber optic lighting supply to said projection lens mounted distally on said boom;
    whereby said mobile lighting unit may be wheeled into a convenient location for illumination.

13. The mobile videoimaging unit according to claim 12, further comprising a remotely-controlled pan-tilt-zoom video camera mounted distally on one end of said boom, and a color video display connected to said video camera and mounted on said mast for displaying an output from the remotely-controlled video camera to an operator.

* * * * *